(12) United States Patent
Crudden et al.

(10) Patent No.: US 9,492,584 B2
(45) Date of Patent: Nov. 15, 2016

(54) POST-CHARGING OF ZEOLITE DOPED PLASTICS WITH ANTIMICROBIAL METAL IONS

(75) Inventors: Joseph J. Crudden, Hudson, NH (US); Derrick Johns, Austin, TX (US)

(73) Assignee: DiFusion Technologies, Inc., Georgetown, TX (US)

( * ) Notice: Subject to any disclaimer, the term of this patent is extended or adjusted under 35 U.S.C. 154(b) by 0 days.

(21) Appl. No.: 13/511,176

(22) PCT Filed: Nov. 24, 2010

(86) PCT No.: PCT/US2010/058009
§ 371 (c)(1),
(2), (4) Date: Aug. 30, 2012

(87) PCT Pub. No.: WO2011/066391
PCT Pub. Date: Jun. 3, 2011

(65) Prior Publication Data
US 2012/0315340 A1    Dec. 13, 2012

Related U.S. Application Data

(60) Provisional application No. 61/264,289, filed on Nov. 25, 2009, provisional application No. 61/300,631, filed on Feb. 2, 2010.

(51) Int. Cl.
*A61L 27/10* (2006.01)
*A61L 27/44* (2006.01)
*A61L 27/54* (2006.01)
*C08L 71/12* (2006.01)

(52) U.S. Cl.
CPC .............. *A61L 27/10* (2013.01); *A61L 27/446* (2013.01); *A61L 27/54* (2013.01); *A61L 2300/404* (2013.01)

(58) Field of Classification Search
CPC ............... A26L 27/10; A26L 27/446; A26L 27/54; A26L 2300/404; C08L 71/12
USPC ............. 424/618, 684; 623/11, 16.11, 17.17, 623/17.18, 17.19, 23.56, 23.59; 604/890.1, 604/892.1; 423/700
See application file for complete search history.

(56) References Cited

U.S. PATENT DOCUMENTS

| | | | |
|---|---|---|---|
| 4,088,737 A | 5/1978 | Thomas et al. | |
| 4,596,574 A | 6/1986 | Urist | |
| 4,612,337 A | 9/1986 | Fox, Jr. et al. | |
| 4,615,705 A | 10/1986 | Scales et al. | |
| 4,775,585 A * | 10/1988 | Hagiwara | A01N 25/34 428/323 |
| 4,775,586 A | 10/1988 | Bohrn et al. | |
| 4,861,808 A | 8/1989 | Billington et al. | |
| 4,906,464 A | 3/1990 | Yamamoto et al. | |
| 4,911,898 A | 3/1990 | Hagiwara et al. | |
| 4,911,899 A | 3/1990 | Hagiwara et al. | |
| 4,923,450 A | 5/1990 | Maeda et al. | |
| 4,938,955 A | 7/1990 | Niira et al. | |
| 4,938,958 A | 7/1990 | Niira et al. | |
| 4,957,817 A | 9/1990 | Chau et al. | |
| 4,959,268 A * | 9/1990 | Hagiwara | A01N 59/16 428/403 |
| 5,003,638 A | 4/1991 | Miyake et al. | |
| 5,100,671 A | 3/1992 | Maeda et al. | |
| 5,151,122 A | 9/1992 | Atsumi et al. | |
| 5,180,585 A | 1/1993 | Jacobson et al. | |
| 5,192,590 A | 3/1993 | Sherman | |
| 5,256,390 A | 10/1993 | Hu | |
| 5,266,534 A | 11/1993 | Atsumi et al. | |
| 5,294,634 A | 3/1994 | Yamaguchi | |
| 5,296,238 A | 3/1994 | Sugiura et al. | |
| 5,474,797 A | 12/1995 | Sioshansi et al. | |
| 5,478,563 A | 12/1995 | Erami | |
| 5,492,763 A | 2/1996 | Barry et al. | |
| 5,522,904 A | 6/1996 | Moran et al. | |
| 5,556,699 A | 9/1996 | Niira et al. | |
| 5,595,750 A | 1/1997 | Jacobson et al. | |
| 5,607,464 A | 3/1997 | Trescony et al. | |
| 5,609,629 A | 3/1997 | Fearnot et al. | |

(Continued)

FOREIGN PATENT DOCUMENTS

| | | |
|---|---|---|
| BY | 11260 C1 | 10/2008 |
| CA | 2171703 A1 | 4/1995 |

(Continued)

OTHER PUBLICATIONS

Kurtz et al., "PEEK biomaterials in trauma, orthopedic, and spinal implants," 2007, Biomaterials, 28:4845-4869/.*
Kurtz et al., "PEEK biomaterials in trauma, orthopedic, and spinal implants," 2007; Biomaterials, 28:4845-4869.*
European communication dated Oct. 7, 2015 in co-pending European patent application No. 15163787.3.
Korean communication, with English translation, dated Jan. 12, 2016 in co-pending Korean patent application No. 10-2011-7023593.
Chinese communication, with English translation, issued Sep. 30, 2014 in corresponding Chinese patent application No. 201080062338.X.
Russian Communication, with English translation, issued Jan. 12, 2015 in corresponding Russian patent application No. 2012126078/15(040280).
European communication dated May 27, 2015 in co-pending European patent application No. 10836743.4.

(Continued)

*Primary Examiner* — Jane C Oswecki
(74) *Attorney, Agent, or Firm* — Nields, Lemack & Frame, LLC

(57) ABSTRACT

Methods of post-loading ceramic particles with antimicrobial metal cations are disclosed. In certain embodiments, the post-loaded particles are zeolites, wherein the zeolites have been incorporated into a resin and the combination is used as an implantable device. In certain embodiments, the polymer is a thermoplastic polymer such as polyaryletheretherketone (PEEK). In certain embodiments, the source of antimicrobial activity includes ion-exchangeable cations contained in a zeolite. In certain embodiments, disclosed are methods of imparting antimicrobial activity to devices by controlling the delivery of certain cations through ion-exchange via a zeolite incorporated in the device.

10 Claims, No Drawings

(56) References Cited

U.S. PATENT DOCUMENTS

| | | | |
|---|---|---|---|
| 5,614,568 A | 3/1997 | Mawatari et al. | |
| 5,647,858 A | 7/1997 | Davidson | |
| 5,688,561 A | 11/1997 | Ichikawa et al. | |
| 5,709,870 A | 1/1998 | Yoshimura et al. | |
| 5,731,087 A | 3/1998 | Fan et al. | |
| 5,753,251 A | 5/1998 | Burrell et al. | |
| 5,756,145 A | 5/1998 | Darouiche | |
| 5,770,255 A | 6/1998 | Burrell et al. | |
| 5,783,570 A | 7/1998 | Yokota et al. | |
| 6,015,816 A | 1/2000 | Kostyniak et al. | |
| 6,090,732 A | 7/2000 | Ito et al. | |
| 6,180,606 B1 | 1/2001 | Chen et al. | |
| 6,248,342 B1 | 6/2001 | Trogolo et al. | |
| 6,267,590 B1 | 7/2001 | Barry et al. | |
| 6,296,863 B1 | 10/2001 | Trogolo et al. | |
| 6,436,422 B1 | 8/2002 | Trogolo et al. | |
| 6,471,993 B1 | 10/2002 | Shastri et al. | |
| 6,582,715 B1 * | 6/2003 | Barry | A61L 27/02 424/422 |
| 6,585,767 B1 | 7/2003 | Holley et al. | |
| 6,720,006 B2 | 4/2004 | Hanke et al. | |
| 6,723,428 B1 | 4/2004 | Foss et al. | |
| 6,866,859 B2 | 3/2005 | Trogolo et al. | |
| 6,946,196 B2 | 9/2005 | Foss | |
| 6,984,392 B2 | 1/2006 | Bechert et al. | |
| 6,994,883 B2 * | 2/2006 | Layrolle | A61F 2/30767 427/2.27 |
| 7,270,813 B2 | 9/2007 | Shimp et al. | |
| 7,354,605 B2 | 4/2008 | Trogolo et al. | |
| 7,357,949 B2 | 4/2008 | Trogolo et al. | |
| 8,652,645 B2 | 2/2014 | Dingeldein et al. | |
| 8,821,912 B2 * | 9/2014 | Crudden | A61L 27/18 424/423 |
| 8,840,914 B2 * | 9/2014 | Crudden | A61L 27/18 424/423 |
| 9,107,765 B2 | 8/2015 | Ghiselli et al. | |
| 9,132,576 B2 | 9/2015 | Crudden et al. | |
| 2002/0099449 A1 | 7/2002 | Speitling | |
| 2003/0031687 A1 | 2/2003 | Falder et al. | |
| 2004/0109937 A1 | 6/2004 | Jennissen et al. | |
| 2005/0058682 A1 | 3/2005 | Sharratt | |
| 2005/0064176 A1 | 3/2005 | Terry | |
| 2005/0149196 A1 | 7/2005 | Zucherman et al. | |
| 2005/0170070 A1 | 8/2005 | Layrolle et al. | |
| 2005/0203529 A1 | 9/2005 | Boehm, Jr. et al. | |
| 2006/0052479 A1 | 3/2006 | Cougoulic | |
| 2006/0069438 A1 | 3/2006 | Zucherman et al. | |
| 2006/0161256 A1 | 7/2006 | Ziegler et al. | |
| 2006/0177379 A1 | 8/2006 | Asgari | |
| 2006/0259020 A1 * | 11/2006 | Sharratt | A01N 25/34 606/1 |
| 2006/0265065 A1 | 11/2006 | Bagga et al. | |
| 2006/0280803 A1 | 12/2006 | Kumar et al. | |
| 2007/0015110 A1 | 1/2007 | Zhang et al. | |
| 2007/0031515 A1 | 2/2007 | Stucky et al. | |
| 2007/0110825 A1 | 5/2007 | Taniguchi et al. | |
| 2007/0267029 A1 | 11/2007 | Mason | |
| 2007/0276337 A1 | 11/2007 | Trieu | |
| 2007/0299472 A1 | 12/2007 | Brighton | |
| 2008/0032119 A1 * | 2/2008 | Feldhahn | A61M 16/06 428/332 |
| 2008/0033572 A1 | 2/2008 | D'Antonio et al. | |
| 2008/0063671 A1 | 3/2008 | Morris et al. | |
| 2008/0208340 A1 | 8/2008 | Boyd et al. | |
| 2008/0249637 A1 | 10/2008 | Asgari | |
| 2008/0258337 A1 | 10/2008 | Ajbani et al. | |
| 2009/0012612 A1 | 1/2009 | White et al. | |
| 2009/0238850 A1 | 9/2009 | Greener | |
| 2010/0010632 A1 | 1/2010 | Bourges et al. | |
| 2010/0099058 A1 | 4/2010 | Wang | |
| 2010/0114317 A1 | 5/2010 | Lambrecht et al. | |
| 2010/0215643 A1 | 8/2010 | Clevenger et al. | |
| 2011/0022181 A1 | 1/2011 | Kasahara et al. | |
| 2012/0141599 A1 | 6/2012 | Johns et al. | |
| 2012/0323339 A1 | 12/2012 | Olalde Graells et al. | |
| 2013/0004585 A1 | 1/2013 | Crudden et al. | |
| 2013/0037991 A1 | 2/2013 | Crudden et al. | |
| 2013/0073042 A1 | 3/2013 | Ghiselli et al. | |
| 2014/0366362 A1 | 12/2014 | Crudden et al. | |
| 2015/0342747 A1 | 12/2015 | Whang et al. | |

FOREIGN PATENT DOCUMENTS

| | | | |
|---|---|---|---|
| CN | 1732025 A | 2/2006 | |
| CN | 100360193 C | 1/2008 | |
| CN | 101234304 A | 8/2008 | |
| CN | 101234304 A * | 8/2008 | ............ B01D 71/52 |
| CN | 101238166 A | 8/2008 | |
| DE | 3228849 A1 | 2/1984 | |
| DE | 10055465 A1 | 5/2002 | |
| EA | 011594 B1 | 4/2009 | |
| EP | 0116865 A1 | 8/1984 | |
| EP | 0253663 A2 | 1/1988 | |
| EP | 0722660 A2 | 7/1996 | |
| EP | 1813292 A1 | 8/2007 | |
| FR | 2848856 A1 | 6/2004 | |
| JP | 2512324 B2 | 7/1996 | |
| JP | 2003-513682 A | 4/2003 | |
| JP | 2004-523302 A | 8/2004 | |
| KR | 10-2009-0031668 A | 3/2009 | |
| RU | 2313370 C2 | 12/2007 | |
| RU | 2338557 C2 | 11/2008 | |
| WO | 84/01721 A1 | 5/1984 | |
| WO | 99/07326 A2 | 2/1999 | |
| WO | 00/30697 A1 | 6/2000 | |
| WO | 00/32247 A2 | 6/2000 | |
| WO | 00/64505 A1 | 11/2000 | |
| WO | 03/086495 A1 | 10/2003 | |
| WO | 2004/058319 A1 | 7/2004 | |
| WO | 2006/069677 A2 | 7/2006 | |
| WO | 2007/019461 A2 | 2/2007 | |
| WO | 2008/037751 A2 | 4/2008 | |
| WO | 2008/039488 A2 | 4/2008 | |
| WO | 2008/150867 A2 | 12/2008 | |
| WO | 2009/099559 A2 | 8/2009 | |
| WO | WO2009/099559 A2 * | 8/2009 | ............ A61F 2/02 |
| WO | 2010/114827 A1 | 10/2010 | |
| WO | 2014/152649 A1 | 9/2014 | |

OTHER PUBLICATIONS

European communication dated Oct. 27, 2015 in co-pending European patent application No. 10836743.4.

Chinese communication, with English translation, mailed Mar. 30, 2015 in co-pending Chinese patent application No. 201180023035.1.

Mexican communication, with English translation, dated Apr. 17, 2015 in co-pending Mexican patent application No. MX/a/2012/012710.

Chinese communication, with English translation, dated Oct. 10, 2015 in co-pending Chinese patent application No. 201180023035.1.

Russian communication, with English Translation, dated Dec. 28, 2015 in co-pending Russian patent application No. 2012152640.

International Search Report and Written Opinion mailed Jul. 21, 2014 in co-pending PCT application No. PCT/US14/27576.

International Preliminary Report on Patentability mailed Apr. 8, 2015 in co-pending PCT application No. PCT/US14/27576.

Journal of the Brazilian Chemical Society, vol. 19,. No. 1, Sao Paolo, 2008, pp. 1-11, downloaded from the interenet Mar. 1, 2013, "Preparation and characterization of poly(ether ether ketone) derivatives", Conceicao, et al.

Net Motion, Inc., copyright 2003, http://www.netmotion.com/htm_files/wh_properties.htm#chem, pp. 1-8, downloaded from internet Mar. 1, 2013, All you want to know about Polyetheretherketone (PEEK), Chemical Resistance of PEEK, PEEK and Polymer chemical resistance.

Zinc Toxicity in Humans, 2007, Elsevier B.V. publication, pp. 1-7, Jerome Nriagu, School of Public Health, University of Michigan.

(56) References Cited

OTHER PUBLICATIONS

29th Edition of the Kunststoff Taschenbuch, 2004, pp. 514-517, Oberbach, et al.
VICI AG International, 2013, VICI JOUR—Technical Support, Chemical Resistance of PEEK and Other Polymers, Chart displaying PEEK and Polymer Chemical Resistance, 3 pages.
The Structure and Synthesis of Zeolite Molecular Sieves, Jilin University Press, Aug. 1987, 1st Edition, pp. 6 and 8, 4 pages, Xu, et al.
Final rejection mailed Oct. 16, 2014 in co-pending U.S. Appl. No. 13/260,571.
Office action mailed Apr. 22, 2015 in co-pending U.S. Appl. No. 13/260,571.
Final rejection mailed Nov. 17, 2015 in co-pending U.S. Appl. No. 13/260,571.
Notice of Allowance mailed Jan. 15, 2016 in co-pending U.S. Appl. No. 14/823,063.
Extended European Search Report mailed May 21, 2013 in corresponding European patent application No. EP 10833925.0.
European communication mailed Feb. 6, 2014 in co-pending European patent application No. 10759287.5.
Chinese communication, with English translation, issued Jul. 1, 2014 in corresponding Chinese patent application No. 201080062338.X.
Chinese communication, with English translation, issued Jun. 17, 2014 in co-pending Chinese patent application No. CN 201080063584.7.
Chinese communication, with English translation, issued Jul. 7, 2014 in co-pending Chinese patent application No. CN 201180023035.1.
Notice of Allowance mailed May 29, 2014 in co-pending U.S. Appl. No. 13/512,702.
Notice of Allowance mailed Jul. 14, 2014 in co-pending U.S. Appl. No. 13/512,702.
Notice of Allowance mailed Jun. 12, 2014 in co-pending U.S. Appl. No. 13/653,896.
Miscellaneous communication mailed Aug. 6, 2014 in co-pending U.S. Appl. No. 13/653,896.
Supplemental Notice of Allowability mailed Aug. 13, 2014 in co-pending U.S. Appl. No. 13/653,896.
International Search Report and Written Opinion mailed Aug. 25, 2011 in co-pending PCT application No. PCT/US2010/059868.
International Preliminary Report on Patentability mailed Jun. 21, 2012 in co-pending PCT application No. PCT/US2010/059868.
International Search Report and Written Opinion mailed Aug. 19, 2011 in corresponding PCT application No. PCT/US2010/058009.
International Preliminary Report on Patentability mailed Jun. 7, 2012 in corresponding PCT application No. PCT/US2010/058009.
Neurosurg. Focus, vol. 10, No. 4, 2001, 7 pages, "Bone Graft Substitutes for the Promotion of Spinal Arthrodesis", Helm, et al.
Russian communication, with English translation, dated Sep. 15, 2014 in corresponding Russian patent application No. 2012126078/15(040280).
Office Action mailed Oct. 8, 2014 in co-pending U.S. Appl. No. 14/471,329.
Office Action mailed Oct. 9, 2014 in co-pending U.S. Appl. No. 13/696,346.
European Communication mailed Aug. 27, 2013 in co-pending European patent application No. EP 10836743.4.
English translation of Chinese Communication issued Oct. 30, 2013 in co-pending Chinese patent application No. CN 201080063584.7.
Russian Communication, with English translation, issued Nov. 20, 2013 in co-pending Russian patent application No. RU 2012129171.
European Communication mailed Sep. 4, 2013 in co-pending European patent application No. EP 11778401.7.
Antimicrobial Agents and Chemotherapy, Dec. 2005, vol. 49, No. 12, p. 4853-4859, "Role of Silver Ions in Destabilization of Intermolecular Adhesion Forces Measured by Atomic Force Microscopy in *Staphylococcus epidermidis* Biofilms", Chaw, et al.
Clinical Microbiology Reviews, Apr. 2002, vol. 15, No. 2, pp. 155-166, Focus, "Bacterial Adhesion: Seen Any Good Biofilms Lately?", Dunne, Jr., et al.
J Bone Miner Res., Nov. 1992, vol. 7(11), pp. 1281-1289, 1 page Abstract, http://www.ncbi.nlm.nih.gov/pubmed/1334616, "Zeolite A increases proliferation, differentiation, and transforming growth factor beta production in normal adult human osteoblast-like cells in vitro", Keeting, et al.
Medical Design Technology Online, Jan. 28, 2010, 5 pages, http://www.mdtmag.com/scripts/ShowPR.asp?PUBCODE=046&ACCT=0006305&ISSUE . . . , "Taking a PEEK at Material Options for Orthopedics", Kinbrum.
Journal of Polymer Science: Part B: Polymer Physics, 2004, vol. 42, pp. 1548-1563, "Poly(ether ether ketone)/Poly(aryl ether sulfone) Blends: Melt Rheological Behavior", Nandan, et al.
Final Rejection mailed Jul. 17, 2013 in co-pending U.S. Appl. No. 13/512,702.
Office Action mailed Dec. 11, 2013 in co-pending U.S. Appl. No. 13/653,896.
International Search Report/Written Opinion mailed May 13, 2010 in co-pending PCT application No. PCT/US10/29180.
International Preliminary Report on Patentability dated Dec. 6, 2011 in co-pending PCT application No. PCT/US 10/29180.
Chinese Communication issued Sep. 26, 2012 in co-pending Chinese patent application No. CN 201080015851.3.
Russian Communication, with English translation, issued Oct. 9, 2013 in co-pending Russian patent application No. RU 2011144020.
DiFusion Technologies research paper, created Oct. 14, 2013, "Novel Orthopedic Implant Material Protects Osteoblast Viability in the Presence of Biofilm-Forming MRSA", 4 pages.
Emerging Infectious Diseases, vol. 7, No. 2, Mar.-Apr. 2001, pp. 277-281, "Biofilms and Device-Associated Infections", Donlan.
"Antimicrobial Efficacy of a novel Orthobiologic PEEK in treating Surgical Site Spine Infections", http://www.difusiontech.com/wp-content/uploads/NASS-Summer-Conference_2013-Abstract_final2.pdf, NASS Summer Session, Aug. 2-5, 2013, Naples, FL, 2 pages, Eastlack, et al.
"Exploring the efficacy of a self-sterilizing orthobiologic PEEK as a viable biomaterial for spinal surgery", http://www.nassannualmeeting.org/Documents/AMB_FinalProgram.pdf, Abstract, NASS Annual Meeting, Oct. 9-12, 2013 NewOrleans, LA, 3 pages, Eastlack, et al.
The Journal of Biological Chemistry, vol. 263, No. 13, May 5, 1988, pp. 6276-6280, "Regulation of the Enterotoxin B Gene in *Staphylococcus aureus*", Gaskill, et al.
Ann Nutr Metab., 1993, 37(5):245-252, 2 page abstract, "Impaired mechanical strength of bone in experimental copper deficiency", Jonas, et al.
European Cells and Materials, vol. 8, 2004, pp. 37-57, "Concise Review of Mechanisms of Bacterial Adhesion to Biomaterials and of Techniques Used in Estimating Bacteria-Material Interactions", Katsikogianni, et al.
Clin. Orthop. Relat. Res., Nov.-Dec. 1981, vol. 161, pp. 154-162, 1 page Abstract, "Antibacterial and osteoinductive properties of demineralized bone matrix treated with silver", Kramer, et al.
Medicaldevice-network.com, Jul. 2011, http://www.medicaldevice-network.com/features/feature128303, "PEEK performance: A next-generation biomaterial", 5 pages, Kurtz.
The Journal of Nutrition, 2002, http://jn.nutrition.org/content/132/10/3135.full.pdf+html, Nutrient Requirements, "Bone Morphology, Strength and Density are Compromised in Iron-Deficient Rats and Exacerbated by Calcium Restriction", pp. 3135-3141, Medeiros, et al.
BMC Musculoskeletal Disorders, 2013, 14:187, http://www.biomedcentral.com/1471-2474/14/187, 11 pages, "*Staphylococcus aureus* biofilms decrease osteoblast viability, inhibits osteogenic differentiation, and increases bone resorption in vitro", Sanchez, Jr., et al.
Rothman-Simeone—The Spine, 6th Edition, vol. II, Chapter 98, Garfin,, S., ed., "Postoperative Spinal Infections", 53 pages, Smith, et al.
United States Environmental Protection Agency, Silver—Copper Zeolite Data Review, Feb. 15, 1994, 3 pages.

(56) References Cited

OTHER PUBLICATIONS

Russian communication dated Apr. 14, 2014 in co-pending Russian patent application No. 2011144020/15.
Russian communication dated Apr. 17, 2014 in co-pending Russian patent application No. 2012129171/15(045686).
Canadian communication dated Apr. 9, 2014 in co-pending Canadian patent application No. 2,795,836.
Journal of the Physical Society of Japan, vol. 77, No. 6, Jun. 2008, 064712, "Photoluminescence of the Dehydrated Ag-type Zeolite A Packed under Air", pp. 064712-1-064712-7, Hoshino, et al.
National Institute of Standards and Technology (NIST) recommended practice guide, Special Publication 960-17, Sep. 2006, "Porosity and Specific Surface Area Measurements for Solid Materials", 91 pages, Klobes, et al.
J. Phys. Chem. A, 2000, vol. 104, pp. 7473-7483, "Colors of Ag+-Exchanged Zeolite A.", Seifert, et al.
Office Action mailed May 12, 2014 in co-pending U.S. Appl. No. 13/260,571.
Chinese Communication issued Jan. 6, 2014 in co-pending Chinese patent application No. CN 201180023035.1.
Chinese Communication issed Dec. 3, 2013 in corresponding Chinese patent application No. CN 201080062338.X.
Office Action—Restriction—mailed Jan. 23, 2014 in co-pending U.S. Appl. No. 13/260,571.
Notice of Allowance mailed Apr. 11, 2016 in co-pending U.S. Appl. No. 14/823,063.
International Search Report and Written Opinion mailed Jan. 9, 2012 in co-pending PCT application No. PCT/US2011/035468.
International Preliminary Report on Patentability mailed Aug. 7, 2012 in co-pending PCT application No. PCT/US2011/035468.
Biomaterials, vol. 28, 2007, pp. 4845-4869, "PEEK biomaterials in trauma, orthopedic, and spinal implants", Kurtz, et al.
Office Action mailed Jan. 10, 2013 in co-pending U.S. Appl. No. 13/512,702.

\* cited by examiner

POST-CHARGING OF ZEOLITE DOPED PLASTICS WITH ANTIMICROBIAL METAL IONS

This application claims priority of U.S. Provisional Application Ser. No. 61/264,289 filed Nov. 25, 2009 and U.S. Provisional Application Ser. No. 61/300,631 filed Feb. 2, 2010, the disclosure of which are incorporated herein.

BACKGROUND

Implantable medical devices are implanted into the body for various reasons, including orthopedics (e.g., hip replacement, spinal procedures, knee replacement, bone fracture repair, etc. In view of the structural integrity requirements of such devices, materials of fabrication are limited, and conventionally include metal, plastic and composites.

The benefits derived from these devices are often offset by infection, which can lead to sepsis and death. The most common organisms causing infections are *Staphylococcus epidermidis* and *Staphylococcus aureus*. Other gram-positive bacteria, gram-negative bacteria and fungal organisms also are problematic. Of particular concern is Methicillin-resistant *Staphylococcus aureus* (MRSA), a type of *staphylococcus* bacteria that are resistant to many antibiotics. As a result, MRSA infections are more difficult to treat than ordinary staph infections, and have become a serious problem.

Many pathogenic bacteria can form multicellular coatings, called biofilms on bioengineered implants. Biofilms can facilitate the proliferation and transmission of microorganisms by providing a stable protective environment. These biofilms, when well developed, can disseminate bacterial planktonic showers which can result in broad systemic infection.

Bioengineered materials act as excellent hosts for the formation of bacterial biofilms. Occasionally, (the implant itself carries the infecting organism) implants develop very tenacious biofilms seeded by infecting organisms. When this occurs, usually the implant must be removed, the patient must be treated with a prolonged course of one or more antibiotics in an effort to cure the infection, and a new implant is then re-implanted. This obviously subjects the patient to additional trauma and pain, and is extremely expensive.

Accordingly, much research has been devoted toward preventing colonization of bacterial and fungal organisms on the surfaces of orthopedic implants by the use of antimicrobial agents, such as antibiotics, bound to the surface of the materials employed in such devices. For example, silver is a powerful, natural antibiotic and preventative against infections. Acting as a catalyst, it disables the enzyme that one-cell bacteria, viruses and fungi need for their oxygen metabolism. They suffocate without corresponding harm occurring to human enzymes or parts of the human body chemistry. The result is the destruction of disease-causing organisms in the body. Silver disrupts bacteria membranes, inter-membrane enzymes, and DNA transcription.

Ceramics such as zeolite function as a cation cage, being able to be loaded with silver and other cations having antimicrobial properties. Metal zeolites can be used as an antimicrobial agent, such as by being mixed with the resins used as thermoplastic materials to make the implantable devices, or as coatings to be applied to the devices; see, for example, U.S. Pat. No. 6,582,715, the disclosure of which is hereby incorporated by reference. The antimicrobial metal zeolites can be prepared by replacing all or part of the ion-exchangeable ions in zeolite with ammonium ions and antimicrobial metal ions. Preferably, not all of the ion-exchangeable ions are replaced.

One particular thermoplastic resin that has been found to be useful in an implant is polyetheretherketone (PEEK). PEEK is suitable because its modulus closely matches that of bone. It is possible, under conditions of high temperature and high shear, to incorporate antimicrobial zeolite, such as silver zeolite, into PEEK, such as by mixing doped metal zeolites into molten PEEK (melting point between 300 and 400° C.), followed by molding and processing of the composite blend. Pure PEEK is very light tan and silver zeolite is white. However, the heated melt after processing becomes a dark brown color. The reasons for color development may include oxidation of some of the silver to silver oxides, which may be less soluble and less effective than pure silver cation attached to the zeolite cage. Silver metal can have catalytic properties and may cause breakdown and partial decomposition of the PEEK polymer. Grades of PEEK approved for implantation are very pure and inert and need to pass stringent cytotoxicity testing before being allowed to be implanted into mammals.

The ISO 10993 set entails a series of standards for evaluating the biocompatibility of a medical device prior to a clinical study. These documents were preceded by the Tripartite agreement and are a part of the harmonization of the safe use evaluation of medical devices. Those standards include:

ISO 10993-1:2003 Biological evaluation of medical devices Part 1: Evaluation and testing ISO 10993-2:2006 Biological evaluation of medical devices Part 2: Animal welfare requirements ISO 10993-3:2003 Biological evaluation of medical devices Part 3: Tests for genotoxicity, carcinogenicity and reproductive toxicity ISO 10993-4:2002/Amd 1:2006 Biological evaluation of medical devices Part 4: Selection of tests for interactions with blood ISO 10993-5:2009 Biological evaluation of medical devices Part 5: Tests for in vitro cytotoxicity ISO 10993-6:2007 Biological evaluation of medical devices Part 6: Tests for local effects after implantation ISO 10993-7:1995 Biological evaluation of medical devices Part 7: Ethylene oxide sterilization residuals ISO 10993-8:2001 Biological evaluation of medical devices Part 8: Selection of reference materials ISO 10993-9:1999 Biological evaluation of medical devices Part 9: Framework for identification and quantification of potential degradation products ISO 10993-10:2002/Amd 1:2006 Biological evaluation of medical devices Part 10: Tests for irritation and delayed-type hypersensitivity ISO 10993-11:2006 Biological evaluation of medical devices Part 11: Tests for systemic toxicity ISO 10993-12:2007 Biological evaluation of medical devices Part 12: Sample preparation and reference materials (available in English only)

ISO 10993-13:1998 Biological evaluation of medical devices Part 13: Identification and quantification of degradation products from polymeric medical devices ISO 10993-14:2001 Biological evaluation of medical devices Part 14: Identification and quantification of degradation products from ceramics ISO 10993-15:2000 Biological evaluation of medical devices Part 15: Identification and quantification of degradation products from metals and alloys ISO 10993-16:1997 Biological evaluation of medical devices Part 16: Toxicokinetic study design for degradation products and leachables ISO 10993-17:2002 Biological evaluation of medical devices Part 17: Establishment of allowable limits for leachable substances ISO 10993-18:2005 Biological evaluation of medical devices Part 18: Chemical characterization of materials ISO/TS 10993-19:2006 Biological evaluation of medical devices Part 19: Physio-chemical, morphological and topographical characterization of materials ISO/TS 10993-20:2006 Biological evaluation of medical devices Part 20: Principles and methods for immunotoxicology testing of medical devices There is a possibility that reactions catalyzed by silver while silver zeolite is being incorporated into PEEK, at high temperature, could generate toxic materials which could cause the product to fail these tests. Further still, at these high processing temperatures, metal zeolite can release moisture if it is not extremely dry. This moisture can cause the formation of voids in the polymer melt and can contribute to the decomposition of the PEEK polymer and to oxidation of metals, such as silver, copper and/or zinc, incorporated into the zeolite antimicrobial. Although the presence of voids may not be critical for certain non-load bearing applications, the absence of voids is critical for load-bearing applications such as spinal repair.

If the process of incorporating metal zeolites is carried out in air, severe oxidation can occur as the temperature is raised, and moisture and oxygen come into contact with the metal ions. Silver will rapidly darken to a dark brown or black color. Also, the incorporation of significant quantities of metal zeolites into the PEEK polymer can affect the viscosity and rheology of the composition.

Accordingly, it would be desirable to provide medical devices with effective antimicrobial activity in order to reduce the growth of bacteria and risk of infection that do not suffer from the aforementioned drawbacks.

SUMMARY

The shortcomings of the prior art have been overcome by the embodiments disclosed herein, which relate to devices, such as surgical implants, having antimicrobial properties produced by an inorganic antimicrobial agent, and methods of post-loading ceramic particles with antimicrobial metal cations after the ceramic has been incorporated into the plastic, and is preferably allowed to cool and set in its final shape, which can be achieved by injection molding or by cutting and machining. In certain embodiments, the devices are orthopedic implants. In certain embodiments, the antimicrobial agent is a ceramic species, preferably a metal zeolite. In certain embodiments, the device includes a polymer. In certain embodiments, the polymer is polyaryletheretherketone (PEEK). In certain embodiments, the source of antimicrobial activity includes ion-exchangeable cations contained in a zeolite. In certain embodiments, disclosed are methods of imparting antimicrobial activity to devices by controlling the delivery of certain cations through ion-exchange via a zeolite incorporated in the device introduced in a patient. In certain embodiments, the metal cation is present at a level below the ion-exchange capacity in at least a portion of the zeolite particles.

In certain embodiments, the zeolite is incorporated into the device and surface exposed zeolite is charged with metal ions from one or more aqueous solutions as a source of one or more metal ions. The device is introduced into the body surgically. The rate of release is governed by the extent of loading of the PEEK with zeolite and the extent to which the exposed zeolite is charged with metal ions. The electrolyte concentration in blood and body fluids is relatively constant and will cause ion exchange with ions such as silver, copper and zinc, etc. from the surface of the implant, which deactivate or kill gram positive and gram negative organisms, including *E. coli* and *Staphylococcus aureus*. Effective antimicrobial control (e.g., a six log reduction of microorganisms) is achieved even at low metal ion concentrations of 40 ppb. Radio opacity when viewed under X-ray was retained.

DETAILED DESCRIPTION

Embodiments disclosed herein relate to the use of ceramics, preferably zeolites, as a cation cage in combination with medical implants to deliver and dose one or more antimicrobial cations. Suitable cations include silver, copper, zinc, mercury, tin, lead, gold, bismuth, cadmium, chromium and thallium ions, with silver, zinc and/or copper being preferred, and silver being especially preferred.

Either natural zeolites or synthetic zeolites can be used to make the zeolites used in the embodiments disclosed herein. "Zeolite" is an aluminosilicate having a three dimensional skeletal structure that is represented by the formula: $XM_{2/n}O.Al_2O_3.YsiO_2.ZH_2O$, wherein M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite.

Zeolites can be incorporated into masterbatches of a range of polymers. For final incorporation into PEEK, a masterbatch should be produced by incorporating typically about 20% zeolite. When provided in this form, the pellets of masterbatch PEEK containing the zeolite particles can be further reduced by mixing with more virgin PEEK at high temperature and under high shear. If metal were present in the zeolite, this would result in yet a second exposure to conditions which could cause deterioration of the product.

Other suitable resins include low density polyethylene, polypropylene, ultra high molecular weight polyethylene or polystyrene, polyvinyl chloride, ABS resins, silicones, rubber, and mixtures thereof, and reinforced resins, such as ceramic or carbon fiber-reinforced resins, particularly carbon fiber-reinforced PEEK. The latter can be produced by dispersing the reinforcing material or materials (e.g., carbon fibers) in the polymer matrix, such as by twin screw compounding of implantable PEEK polymer with carbon fibers. The resulting carbon fiber-reinforced product can be used to direct injection mold final devices and near net shapes, or it can be extruded into stock shapes for machining. The incorporation of fibers or other suitable reinforcing material(s) provides high wear resistance, a Young's modulus of 12 GPa (matching the modulus of cortical bone) and providing sufficient strength to permit its use in very thin implant designs which distribute the stress more efficiently to the bone. The amount of reinforcing material such as carbon fiber incorporated into the resin such as PEEK can be varied, such as to modify the Young's modulus and flexural strength. One suitable amount is 30 wt% carbon fiber. The resins also can be made porous, such as porous PEEK, PAEK and PEKK, with suitable porosities including porosities between 50% and 85% by volume. Average pore size is generally greater than 180 microns in diameter, suitably between about 300 and about 700 microns. Porosity can be imparted using a pore forming agent such as sodium chloride, to create a porous polymer comprising a plurality of interconnected pores, by processes known in the art. Each of the foregoing can be formulated to contain suitable amounts of zeolite particles, usually about 20 wt % An UHMWPE (ultra high molecular weight polyethylene) is preferred for the implant devices.

Typical amounts of zeolite particles incorporated in an implant resin range from 0.01 to 50 wt. %, more preferably 0.01 to 8.0 wt. %, most preferably 0.1 to 5.0 wt. %. If an implant is coated with a coating or resin which is loaded with zeolite, the coating needs to be applied and dried or cured before the infusion is carried out. The method used to coat an implant is not particularly limited, and can include spraying, painting or dipping. When compounded into a PEEK masterbatch, for example, the PEEK should be protected from sources of moisture and contamination prior to reduction with virgin resin. The compounding can be carried out by blending the molten masterbatch and let down resin under conditions of high temperature and high shear.

The masterbatch is a concentrated mixture of pigments and/or additives (e.g., zeolite powder) encapsulated during a heat process into a carrier resin which is then cooled and cut into a granular shape. Using a masterbatch allows the processor to introduce additives to raw polymer (let down resin) economically and simply during the plastics manufacturing process.

In accordance with certain embodiments, a purer more stable product can be produced by charging the polymer with pure zeolite (e.g., one that is not yet loaded with antimicrobial metal ions, or one that is only partially loaded), such as type X zeolite, available from W.R. Grace & Co.-Conn., which is capable of carrying a cationic metal ion cargo such as $Ag+$, $Cu++$, $Cu+$, or $Zn+$, and subsequently charging the cooled (e.g. cooled to a temperature between about 0 and 100° C., preferably about room temperature) zeolite-containing PEEK surface with metal ions from a metal ion source such as an aqueous metal ion solution, such as silver nitrate, copper nitrate and zinc nitrate, alone or in combination. Cooling to lower temperatures gives lower loading rates but higher stability. Loading at even higher temperatures can be carried out at a faster rate by maintaining the system under pressure, such as in a pressure cooker or autoclave. The content of the ions can be controlled by adjusting the concentration of each ion species (or salt) in the solution.

By incorporating the metal cation into the zeolite after the zeolite has been incorporated into the polymer resin, oxidation of the metal ions is reduced or eliminated. Those skilled in the art will appreciate that other metal ion salt solutions, such as acetates, benzoates, carbonates, oxides, etc., can be used instead of or in addition to nitrates. Addition of nitric acid to the infusion solution also may be advantageous in that it can etch the surface of the implant, providing additional surface area for ion exchange.

Since PEEK is susceptible to dissolution by strong oxidizing acids, care should be taken to not use too high an acid concentration that may lead to metal zeolite particles being released from the surface. PEEK is very stable and impermeable to water and bodily fluids. As a result, it is expected that metal ions that are incorporated in a zeolite cage dispersed in PEEK will only elute when the cage is exposed at the surface of the polymer. For this reason, it is possible to post incorporate at least as much available metal ions by post treatment from solution as would be available from metal zeolite incorporated into the hot mix. In fact, the availability of metal ions from the post incorporated system is expected to be significantly higher since the metal ions will be pure and will have experienced no thermal oxidation or hot reactions with the polymer.

The amount of metal ions in the zeolite should be sufficient such that they are present in an antimicrobial effective amount. For example, suitable amounts can range from about 0.1 to about 20 or 30% of the exposed zeolite (w/w%). These levels can be determined by complete extraction and determination of metal ion concentration in the extraction solution by atomic absorption.

Preferably the ion-exchanged antimicrobial metal cations are present at a level less than the ion-exchange capacity of the ceramic particles. The amount of ammonium ions is preferably limited to from about 0.5 to about 15 wt. %, more preferably 1.5 to 5 wt. %. For applications where strength is not of the utmost importance the loading of zeolite can be taken as high as 50%. At such loadings the permeation of metal ions can permeate well below the surface layer due to interparticle contact, and much greater loadings of metal ions are possible.

The amount of zeolite incorporated into the resin should also be an amount effective for promoting antimicrobial activity; e.g., a sufficient amount so as to prevent or inhibit the growth of bacterial and/or fungal organisms or preferably to kill the same. Suitable amounts of zeolite in the resin range from about 0.01 to 50.0 wt. %, more preferably from about 0.01 to 8.0 wt. %, most preferably from about 0.1 to about 5.0 wt. %.

The absorption of metal ions into synthetic zeolites, or natural Zeolites, in an aqueous dispersion, or loaded in a polymer can be carried out from solutions of the metal salts. The rates of absorption will be proportional to the area of zeolite surface available, the concentration of metal ions in solution and the temperature. As the concentration of metal absorbed by the zeolite increases, the rate will be reduced. When the rate of absorption reaches the rate of release, equilibrium is reached at that solution concentration. A higher concentration in solution could drive the loading higher. Loaded zeolite can be rinsed with deionized water to completely remove adherent metal ion solution. The objective is to have only ion exchanged metal cations attached to the cage and these will only be removed by ion exchange, not by deionized water.

The most useful ions to incorporate, for the purposes of release into orthopedic implants, are silver, copper and zinc ions. All three have antimicrobial properties, silver being the most active. There also may be synergies between the metals, in terms of antimicrobial activity. For instance, if a microorganism is developing resistance to one metal species, it may still be readily killed by one of the others. Copper and zinc ions also exert further functions in healing and wound repair and bone growth.

For example, the PEEK zeolite composite can be loaded by bringing the material into contact with an aqueous mixed solution containing ammonium ions and antimicrobial metal ions such as silver copper, zinc etc. The most suitable temperatures at which the infusion can be carried out range from 5° C. to 75° C., but higher temperatures may also be used even above 100° C. if the reaction vessel is held under pressure. Higher temperatures will show increased infusion rates but lower temperatures may eventually produce more uniform and higher loadings. The pH of the infusion solution can range from about 2 to about 11 but is preferably from about 4 to about 7.

Suitable sources of ammonium ions include ammonium nitrate, ammonium sulfate and ammonium acetate. Suitable sources of the antimicrobial metal ions include: a silver ion source such as silver nitrate, silver sulfate, silver perchlorate, silver acetate, diamine silver nitrate and diamine silver nitrate; a copper ion source such as copper(II) nitrate, copper sulfate, copper perchlorate, copper acetate, tetracyan copper potassium; a zinc ion source such as zinc(II) nitrate, zinc sulfate, zinc perchlorate, zinc acetate and zinc thiocyanate.

The following are illustrative examples of infusion solutions but a wide range of concentrations and ratios are effective.

Infusion solution A

| Component | Composition (W/W)% |
|---|---|
| Ammonium hydroxide | 2.0 |
| Silver Nitrate | 1.2 |
| Purified water | 96.8 |
| pH can be adjusted with acid such as citric acid or nitric acid | |
| Total | 100 |

Infusion Solution B

| Component | Composition (W/W)% |
|---|---|
| Ammonium hydroxide | 2.0 |
| Copper Nitrate | 5.0 |
| Purified water | 93.0 |
| pH can be adjusted with acid such as citric acid or nitric acid | |
| Total | 100.0 |

Infusion Solution C

| Component | Composition (W/W)% |
|---|---|
| Ammonium hydroxide | 2.0 |
| Zinc Nitrate | 7.0 |
| Purified water | 91.0 |
| pH can be adjusted with acid such as citric acid or nitric acid | |
| Total | 100.0 |

Infusion Solution D

| Component | Composition (W/W)% |
|---|---|
| Ammonium hydroxide | 2.0 |
| Silver Nitrate | 0.5 |
| Copper Nitrate | 2.0 |
| Zinc Nitrate | 2.5 |
| Purified water | 93.0 |
| pH can be adjusted with acid such as citric acid or nitric acid | |
| Total | 100 |

Since there is a delicate balance between the concentrations of silver, zinc and copper in metabolism for optimum healing, an advantage of the current method is that it will provide and easy method for accurately controlling the relative concentrations of the individual metal ions. The optimum ratios can be achieved by varying the concentrations of the various metal ion salts to load at the appropriate ratios and subsequently release at the appropriate ratios and rates.

The rates of release of the metal ions into phosphate buffered saline or for example 0.8% sodium nitrate solution, can be quantified by Inductively Coupled Plasma spectroscopy ICP, or Graphite Furnace Atomic Absorption spectroscopy.

With a ladder study these results can be used to optimize the elution rates. Because the metal ions are never exposed to high temperature, the ions attached and eluting from the zeolite will be pure metal cations.

Another advantage of the current method is that the amount of metal being incorporated into the implant will be limited to just what is incorporated in the surface layer. In terms of cost and safety it is a superior solution.

The process will be effective whether the implants are injection molded or machined to achieve the final dimensions of the implant.

Whereas the process is most applicable to polymers with a high melting point such as PEEK, it could also be used effectively with polymers of lower melting points which are used in a wide range of orthopedic applications. HDPE, for instance, is used in certain elements of hip and knee transplants.

The post loading process is also appropriate for thermoset resins such as polyesters epoxies and urethanes, etc.

This approach will avoid contact of the silver ion with the reactants, reactive intermediates and catalysts which form the finished polymer.

The embodiments disclosed herein are applicable to generating self sterilizing plastic fibers and film. Such materials can be used to produce wound dressings and in a wide array of applications.

Facemasks which elute silver copper and zinc are used to provide long term control of microorganisms which might be inhaled in a medical setting or increasingly in the case of a possible pandemic. Suitable substrates for such devices include polyethylene (PE), polypropylene (PP), polyethylene terephthalate (PET), PCT, PETG (PET, type G), Co-PET and co-polyesters generally, Styrene, polytrimethylene terephalate $(PTT)_m$ 3GT, Halar®, polyamide 6 or 6,6, etc., See U.S. Pat. Nos. 6,946,196 and 6,723,428 to Foss manufacturing, the disclosures of which are incorporated by reference.

Other applications where self sterilizing fabrics or plastic sheeting find application are within the scope of the embodiments disclosed herein.

Where material is exposed or can be immersed, the depleted zeolite can be recharged with antimicrobial metal ions.

It is possible to load a polymer with pure zeolite, extrude the polymer into filaments, and post load the material with the antimicrobial metal ions in the manner described for surgical implants.

Although the focus of the embodiments disclosed herein is on orthopedic implants, those skilled in the art will appreciate that apply to a much wider array of applications, such as toothbrushes, door handles, computer mice and keyboard components, knife handles, and cutting boards, surgical instruments, telephone surface components, water drinking vessels, food storage containers and polymers for producing self sterilizing clothing and self sterilizing face masks.

EXAMPLE 1

An ion exchange zeolite, natural, or synthetic such as zeolite type A or type X commercially available from W.R.

Grace & Co.-Conn., or equivalent, is incorporated into PEEK. Typical amounts of zeolite particles incorporated in an implant resin range from 0.01 to 10 wt. %, more preferably 0.01 to 8.0 wt. %, most preferably 0.1 to 5.0 wt. %. The method used to coat an implant is not particularly limited, and can include spraying, painting or dipping. When compounded into PEEK, for example, the PEEK composite should be protected from sources of moisture and contamination. The compounding can be carried out by blending.

About 5% by weight of the zeolite powder is mixed thoroughly with the powdered or prilled PEEK. The mixture is brought up to temperature and processed at 400° C. using high shear. The zeolite and PEEK must be dry before processing in order to minimize decomposition and void formation in the product.

This system containing Zeolite without added silver ions does not show the progressive color development and darkening which is seen with systems containing silver.

The dark color development in silver zeolite containing systems is thought to be due to silver oxide formation and polymer decomposition.

The material is processed as before and can be formed into prills for further processing, cast into blocks, extruded into rods or injection molded into the final desired shapes.

The block and rod materials can be machined into shapes which are suitable for use as orthopedic implants or other designs where antimicrobial PEEK finds application. Implants can be designed to provide enhanced surface area by having grooves cut in the surfaces or by producing products with holes in the body of the pieces. Surface area can be further enhanced by sanding or abrasive blasting of the surfaces.

EXAMPLE 2

Loading the Finished Pieces with Antimicrobial Metal Ions

Finished pieces produced as described in Example 1 are immersed in an infusion solution to charge the pieces with antimicrobial metal ions.

A typical solution for infusion is produced by adding 2% silver nitrate, 5% copper nitrate trihydrate and 1% nitric acid to purified water.

| Component | Composition (W/W)% |
|---|---|
| Silver Nitrate | 2 |
| Copper nitrate trihydrate | 5 |
| Nitric acid | 1 |
| Purified water | 92 |
| Total | 100 |

The finished pieces are supported or allowed to move freely in the infusion solution. The solution should be agitated to enhance diffusion of ions to and from the surface of the composite. It is advisable to carry out the infusion process in the dark to minimize photo oxidation of the silver in solution. This can be affected on a lab scare by placing an opaque cover such as a tin can over the beaker in which the pieces are being infused.

The rate of infusion depends on several variables. At normal temperatures, 90 minutes is sufficient time to effectively charge the surfaces with metal ions. The infusion process can be allowed to run for 24 hours or more to maximize the antimicrobial metal loading.

The rate and extent of loading depends on several variables, including solution concentration, solution composition, (metal ion ratios), solution temperature, and agitation rate.

It should be possible to load the exposed zeolite to as much as 40% by weight with metal ions.

When infusion is complete or carried out to the desired levels, the pieces are removed from the infusion solution and triply rinsed with purified water. They may then be dried in a stream of hot air or in an oven or desiccator, etc.

A measure of the antimicrobial activity of an article is the antimicrobial metal (e.g., silver) release from the exterior surface of the article. Metal release can be measured as the amount of antimicrobial metal released from the exterior surface of a 2 inch by 2 inch sample (0.05 meter by 0.05 meter, or 5 cm by 5 cm). The exterior surface of the sample to be tested is contacted in a sodium nitrate solution (40 mL of 0.8% sodium nitrate) for 24 hours at room temperature (i.e., 25C) to form a test solution. The test solution is then analyzed to measure the amount of antimicrobial metal in the test solution in parts per billion, and thus the exposure of the inorganic antimicrobial agent at the surface of the article. The amount of antimicrobial metal in the test solution may then be measured using a graphite furnace atomic absorption spectrophotometer or ICP. For an article comprising 2.0 percent by weight (wt. %) of an inorganic antimicrobial agent based on the weight of the article or a layer of a multi-layer article, and wherein the inorganic antimicrobial comprises 2.0 wt % of a antimicrobial metal based on the total weight of the inorganic antimicrobial agent, the exterior surface has a antimicrobial metal release of greater than or equal to about 10 parts per billion (ppb), preferably greater than or equal to about 20 ppb, more preferably greater than or equal to about 30 ppb, and most preferably greater than or equal to about 40 ppb.

What is claimed is:

1. A method of post-charging ceramic particles with antimicrobial metal cations, comprising incorporating uncharged A-type zeolite particles having a three dimensional skeletal structure represented by the formula: $XM_{2/n}O \cdot Al_2O_3 \cdot YSiO_2 \cdot ZH_2O$, wherein M represents an ion-exchangeable ion, n represents the atomic valency of the ion-exchangeable ion, X and Y represent coefficients of a metal oxide of an ion-exchangeable ion and silica dioxide respectively, and Z represents the number of water of crystallization into a thermoplastic polymer, thereafter charging said zeolite particles with one or more metal cations, and establishing the rate of release of said one or more metal ions from said zeolite particles in the thermoplastic polymer; wherein the amount of said uncharged A-type zeolite particles incorporated into said thermoplastic polymer, and the amount of said one or more metal cations charged to said zeolite particles, are effective to achieve antimicrobial activity when said thermoplastic polymer is implanted in the body of a patient and contacts bodily tissue or fluid to release said one or more metal cations from said thermoplastic polymer via ion-exchange.

2. The method of claim 1, wherein said one or more metal cations are selected from the group consisting of silver, zinc and copper.

3. The method of claim 1, further comprising forming said zeolite particles and thermoplastic polymer into an implant having a surface which contacts body tissue or fluid when implanted, and wherein at least some of said zeolite particles are present at said surface and capable of releasing said metal cations in an antimicrobially effective amount.

4. The method of claim 1, wherein said metal cations are present at a level less than the ion-exchange capacity of the zeolite particles.

5. A method of imparting antimicrobial activity to a device by controlling the release of antimicrobial cations from said device through ion-exchange, comprising incorporating A-type zeolite particles having a three dimensional skeletal structure represented by the formula: $XM_{2/n}O \cdot Al_2O_3 \cdot YSiO_2 \cdot ZH_2O$, wherein M represents an ion-exchangeable ion, n represents the atomic valency of the ion-exchangeable ion, X and Y represent coefficients of a metal oxide of an exchangeable ion and silica dioxide respectively, and Z represents the number of water of crystallization into a thermoplastic polymer, subsequently charging said zeolite particles with one or more metal cations, and establishing the rate of release of said one or more metal ions from said zeolite particles in the thermoplastic polymer; wherein the amount of said uncharged A-type zeolite particles incorporated into said thermoplastic polymer, and the amount of said one or more metal cations charged to said zeolite particles, are effective to achieve antimicrobial activity when said thermoplastic polymer is implanted in the body of a patient and contacts bodily tissue or fluid to release said one or more metal cations from said thermoplastic polymer via ion-exchange.

6. The method of claim 5, wherein said metal cations comprise silver.

7. The method of claim 1 or 5, wherein said thermoplastic polymer comprises reinforced PEEK.

8. The method of claim 7, wherein said reinforced PEEK is carbon fiber-reinforced PEEK.

9. The method of claim 1, wherein said thermoplastic polymer comprises PEEK that has a porosity between 50% and 85% by volume of said PEEK.

10. A method of forming an implant which comprises zeolite particles with antimicrobial metal cations, said implant having a surface, said method comprising:
   a. incorporating uncharged A-type zeolite particles having a three dimensional skeletal structure represented by the formula: $XM_{2/n}O \cdot Al_2O_3 \cdot YSiO_2 \cdot ZH_2O$, wherein M represents an ion-exchangeable ion, n represents the atomic valency of the ion-exchangeable ion, X represents a coefficient of a metal oxide of an ion-exchangeable ion and Y represents a coefficient of silica dioxide, and Z represents the number of water of crystallization into a thermoplastic polymer such that at least some of said zeolite particles are present at said implant surface;
   b. forming said zeolite particles and thermoplastic polymer into an implant having a surface which contacts body tissue or fluid when implanted into a living body;
   c. providing an infusion solution comprising antimicrobial metal cation salt and nitric acid;
   d. exposing said implant to said infusion solution to load said zeolite particles with said antimicrobial metal cation and to etch said implant surface with said acid; and
   establishing the rate of release of said one or more metal ions from said zeolite particles in the thermoplastic polymer; wherein said zeolite particles at said implant surface are capable of releasing said metal cations in an antimicrobially effective amount when said surface contacts said body tissue or fluid.

* * * * *